(12) United States Patent
Phung

(10) Patent No.: US 8,287,455 B2
(45) Date of Patent: Oct. 16, 2012

(54) SYNCHRONIZED POWER SUPPLY FOR MEDICAL IMAGING

(75) Inventor: Hue Phung, Cupertino, CA (US)

(73) Assignee: Sonowise, Inc., San Jose, CA (US)

( * ) Notice: Subject to any disclaimer, the term of this patent is extended or adjusted under 35 U.S.C. 154(b) by 1478 days.

(21) Appl. No.: 11/260,766

(22) Filed: Oct. 27, 2005

(65) Prior Publication Data

US 2006/0094960 A1    May 4, 2006

Related U.S. Application Data

(60) Provisional application No. 60/623,729, filed on Oct. 30, 2004.

(51) Int. Cl.
*A61B 8/00* (2006.01)
(52) U.S. Cl. ...................................................... 600/437
(58) Field of Classification Search .................. 600/437, 600/443, 459; 73/1.82, 540
See application file for complete search history.

(56) References Cited

U.S. PATENT DOCUMENTS

| | | | |
|---|---|---|---|
| 4,338,948 A | 7/1982 | Perez-Mendez et al. | |
| 4,455,872 A | 6/1984 | Kossoff et al. | |
| 5,052,394 A | 10/1991 | Carpenter et al. | |
| 5,130,561 A * | 7/1992 | Elliott et al. | 307/31 |
| 5,178,147 A | 1/1993 | Ophir et al. | |
| 5,181,778 A | 1/1993 | Beller | |
| 5,335,209 A | 8/1994 | Jaenke et al. | |
| 5,339,282 A | 8/1994 | Kuhn et al. | |
| 5,435,312 A | 7/1995 | Spivey et al. | |
| 5,437,281 A | 8/1995 | Lin et al. | |
| 5,517,739 A | 5/1996 | Kosinski | |
| 5,549,638 A | 8/1996 | Burdette | |
| 5,551,432 A | 9/1996 | Iezzi | |
| 5,606,971 A | 3/1997 | Sarvazyan | |
| 5,664,573 A | 9/1997 | Shmulewitz | |
| 5,713,356 A | 2/1998 | Kruger | |

(Continued)

FOREIGN PATENT DOCUMENTS

EP    1557125    7/2005

(Continued)

OTHER PUBLICATIONS

Speed of sound, [online] [retrieved on Sep. 23, 2005]. Retrieved from the Internet <URL: http://www.amershamhealth.com/medcyclodaedia/medica/Volume%201/SPEED%200F%20SOUND>.

(Continued)

*Primary Examiner* — Tse Chen
*Assistant Examiner* — Peter Luong
(74) *Attorney, Agent, or Firm* — K&L Gates LLP

(57) ABSTRACT

An ultrasonic image scanning system for scanning an organic object by projecting ultrasound signals with a transmit carrier frequency. The ultrasonic image scanning system includes a switching mode power supply operated with a programmable clock in synchronization with the transmit carrier frequency. The switching mode power supply further provided with circuits for generating a low voltage and a high voltage. The ultrasonic image scanning system further includes transducers for projecting ultrasound signals wherein the transducers are connected to and electrically excited by the high voltage generated by the switching mode power supply. The switching mode power supply further includes a DC-to-DC switcher having an external clock input for clock synchronization. The programmable clock further provided for receiving a user command to operate with the switching mode power supply in synchronization with the transmit carrier frequency

10 Claims, 2 Drawing Sheets

U.S. PATENT DOCUMENTS

| | | | |
|---|---|---|---|
| 6,023,632 | A | 2/2000 | Wilk |
| 6,080,108 | A | 6/2000 | Dunham |
| 6,108,439 | A | 8/2000 | Ishiguro |
| 6,117,080 | A | 9/2000 | Schwartz |
| 6,190,915 | B1 | 2/2001 | Madsen et al. |
| 6,248,071 | B1 | 6/2001 | Lin |
| 6,285,904 | B1 | 9/2001 | Weber et al. |
| 6,287,259 | B1 | 9/2001 | Grunwald |
| 6,322,511 | B1 | 11/2001 | Guracar et al. |
| 6,338,716 | B1 | 1/2002 | Hossack et al. |
| 6,540,681 | B1 | 4/2003 | Cheng et al. |
| 6,547,730 | B1 | 4/2003 | Lin et al. |
| 6,572,546 | B1 * | 6/2003 | Bax et al. .................. 600/437 |
| 6,701,341 | B1 | 3/2004 | Wu et al. |
| 6,780,153 | B2 | 8/2004 | Angelsen et al. |
| 6,783,497 | B2 | 8/2004 | Grenon et al. |
| 6,824,514 | B2 | 11/2004 | Poland et al. |
| 6,839,762 | B1 | 1/2005 | Yu et al. |
| 6,926,672 | B2 | 8/2005 | Moore et al. |
| 6,969,352 | B2 | 11/2005 | Chiang et al. |
| 7,181,665 | B2 * | 2/2007 | Son .............................. 714/742 |
| 7,223,241 | B2 | 5/2007 | Radulescu |
| 7,252,004 | B2 | 8/2007 | Fink et al. |
| 7,266,407 | B2 | 9/2007 | Li et al. |
| 7,578,789 | B2 | 8/2009 | Sandrin et al. |
| 7,628,754 | B2 | 12/2009 | Matsumura et al. |
| 7,708,691 | B2 | 5/2010 | Lin et al. |
| 7,771,355 | B2 | 8/2010 | Lin et al. |
| 2001/0027278 | A1 | 10/2001 | Kaufman et al. |
| 2003/0125625 | A1 | 7/2003 | Kelly et al. |
| 2003/0199765 | A1 | 10/2003 | Stetten et al. |
| 2004/0006272 | A1 | 1/2004 | Vortman et al. |
| 2004/0059221 | A1 | 3/2004 | Azuma et al. |
| 2004/0111028 | A1 | 6/2004 | Abe et al. |
| 2005/0148899 | A1 | 7/2005 | Walker et al. |
| 2005/0251042 | A1 | 11/2005 | Sandrin et al. |
| 2005/0256406 | A1 | 11/2005 | Barthe et al. |
| 2006/0094959 | A1 | 5/2006 | Lin et al. |
| 2006/0094960 | A1 | 5/2006 | Phung |
| 2006/0111634 | A1 | 5/2006 | Wu |
| 2007/0083110 | A1 | 4/2007 | Lin et al. |
| 2007/0276246 | A1 | 11/2007 | Lin |
| 2008/0119735 | A1 | 5/2008 | Lin et al. |
| 2010/0185095 | A1 | 7/2010 | Lin |
| 2010/0280377 | A1 | 11/2010 | Lin et al. |

FOREIGN PATENT DOCUMENTS

| | | |
|---|---|---|
| WO | 2004/041092 | 5/2004 |

OTHER PUBLICATIONS

Burr-Brown PGA 103 Programmable-Gain Amplifier, PDS-1208B, Nov. 1993 (9 pgs.).

Maxim Application Note 429: Programmable-Gain Amplifier, Using the MAX532 DAC, Nov. 1, 2000 (2 pgs.).

* cited by examiner

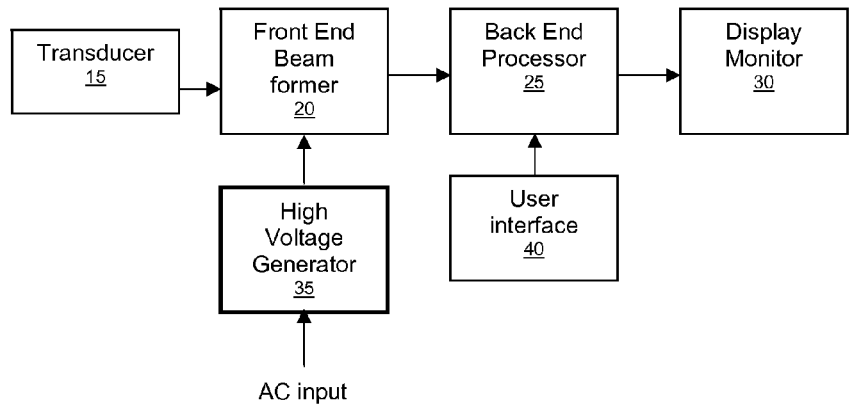
Fig. 1 Conventional ultrasound system
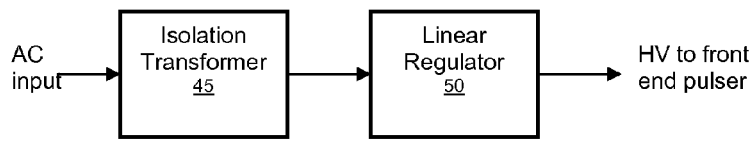
Fig. 2 Prior art high voltage generator with linear regulator
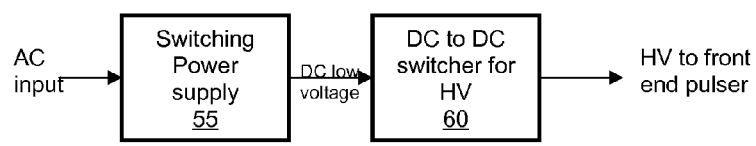
Fig. 3 Prior art high voltage generator with free running clock DC to DC switcher

SYNCHRONIZED POWER SUPPLY FOR MEDICAL IMAGING

This Application is a Formal Application and claims a Priority Filing Date of Oct. 30, 2004 benefited from a previously filed Application No. 60/623,729 filed previously by the inventor of this Patent Application.

FIELD OF THE INVENTION

This invention generally relates to system and method for carrying out a medical imaging process. More particularly, this invention relates to an improved power supply system implemented with a programmable clock synchronization signal generator controlled by a system controller to minimize signal interferences generated by different switching, pulsing and modulation circuits when running with free running clocks.

BACKGROUND OF THE INVENTION

Even though there are significant advancements made in the ultrasound scanning technologies for scanning biological objects to carry out medical image and diagnostic tasks, there are still technical difficulties caused by signal interferences that lead to image degradations.

Specifically, during the transmitting period a high voltage burst pulse, e.g., a 100 Volt burst pulse, is applied to excite the transducer in an ultrasound imaging system to project ultrasound signals into a biological object to perform an image scanning operation. Then the echo signal reflected back from the biological object is received and amplified to construct the tissue image or to detect the blood velocity by applying an analysis using the principle of Doppler effect. However, the echoed signals received from burst to burst are modulated due to the interferences caused by the switching operations of the high voltage power supply interference, e.g., the outgoing burst signals are interrupted by the switching noises thus affecting the echo signals. A two-dimensional scanned image reflected back from the biological tissues thus presents an interference pattern due to these interferences. Furthermore, the interferences also cause the Doppler spectrum to present extra inter-modulation tones. The quality of scanned data and the images constructed from the scanned data are therefore degraded.

Referring to FIG. 1 for a conventional ultrasound system that includes transducer 15 for sending the burst acoustic wave to the body and also receive the echo from the tissue. The ultrasound system further includes a front-end beam former 20 to generate a delay profile of ultrasound waves to focus the beam for both transmitting the ultrasound waves into the biological objects and for receiving the echo signal back to the transducer 15. A high voltage generator 35 receives an AC input from a power source to generate low voltage for the system supply and high voltage for the transducer excitation. Typically, a high voltage for the piezo ceramic transducer is from 30 to 200 volts. The ultrasound system further includes a back end processor 25 to receive signals from the front end processor 20 and also receives user commands from a user interface 40 to perform various back end processes and for generating images for displaying on a display monitor 30.

FIG. 2 is a functional block diagram for showing a conventional high voltage generator for generating the high voltage. The high voltage generator includes an isolation transformer 45 that received an AC input voltage that can be either 110 volts or 220 volts AC input. The isolation transformer 45 performs a step down process to provide a low voltage AC output for the low voltage linear DC regulator. Additionally, the isolation transformer 45 further carried out a step up process to provide output for the high voltage linear regulator. The high and low AC voltages generated from the isolation transformer 45 are processed by a linear regulator 50 to convert the AC to DC voltages for both low voltage i.e. +3.3, +5, +12 V and the high voltage i.e. 150V. The high voltage output is provided to the front-end beam former that includes transmitting pulser for carrying out a transducer excitation function. Since the high voltage generator does not perform a switching function, the high voltage generator 50 does not generate and emit switching noises. The isolation transformer commonly implemented in an ultrasound system is heavy and bulky and also are operated with very low efficiency (e.g. less than 60%).

Referring to FIG. 3 for another conventional approach implemented in a high voltage generator that includes a main switching power supply 55 to receive an AC input and then apply a DC to DC switcher 60 to generate the high voltage for the front end pulser. The DC-to-DC switcher 60 can be optionally implemented as a conventional power supply with switcher followed by a linear regulator. In a conventional system, the common practice is for the DC-to-DC switcher 60 to employ an internal clock that is free running in generating the switching frequency for the high voltage output. Such configuration and circuit implementation however generate a technical difficulty that the DC voltages generated from the free running switching clock create incoherent interferences that affect the receiving echo in many aspects of the system operations. First of all the internal free-running clock generates signals that beat with the system clock. The signals from the free-running switching clock also modulate the wave transmissions emitted from the front-end pulser. Furthermore, the free-running switching clock further interferes with the electric circuits in the front-end receiving beam former and in the transducer shielding. These interferences further degrade the scanned images due to the impacts that these interferences have on the patterns of the two-dimensional images or the inter-mod tones on the Doppler spectrum.

As shown in FIG. 2, in order to avoid the interference problems, the conventional ultrasound imaging systems use Linear Power regulator 50 with step up transformer to generate the High Voltage for the Doppler Ultrasound system. The transformer used in the high voltage linear regulator is heavy and bulky and not suitable for a portable unit. When people use conventional switching mode power Supply for the ultrasound system to improve the efficiency in the portable ultrasound unit, the system usually requires a very significant shielding and a special routing for ground returns to prevent the in-coherent switching noise from getting into the transducer and front end circuitry during receiving. With the latest DC-DC switching technique available in the market, the switching frequency can go up to 400 KHz or higher, and creates various strong harmonics. This new technology increases the power efficiency, reduce the component size, but will create a big challenge in shielding the interference from the switching frequency and its harmonics. The problem is worse in the highly sensitive all digital front end with color Doppler, pulse (PW) and continuous wave (CW) Doppler functions.

Therefore, the conventional ultrasound systems employed to obtain Doppler and image signals are either bulky or become very vulnerable to the interferences by the high voltage switching noises. These interference noises can affect the signals receptions either through the radiation propagated in the system or through the conductive path. Such problems are especially pronounced in the portable color Doppler units due to the very limit space of such device. Special designs to provide layout to shield such interferences become a highly difficult task. In a conventional system, the unit still remains as a cart unit because the linear regulator is still implemented with bulky and heavy shield to prevent interferences. The portability of a color Doppler unit is therefore greatly limited.

For these reasons, a need still exists for those of ordinary skill in the art to provide an improved method and system for medical image scanning operation by applying an ultrasound system. Specifically, it is desirable to provide an improved system design to minimize the effects of signal interferences caused by power supply switching noises.

SUMMARY OF THE INVENTION

It is an aspect of the present invention to provide an improved ultrasound imaging system and method with a programmable and synchronized clock thus without requiring a linear voltage regulator for interference reduction. The embodiment of this invention can significantly reduce the size and weight of the ultrasound system thus enabling a person of ordinary skill to overcome the above-discussed difficulties.

In yet another aspect, the present invention further provides an improved ultrasound imaging system and method with a programmable and synchronized clock for the high voltage switching power supply to substantially eliminate the interference due to the switching noise and its harmonics.

In yet another aspect, the present invention provides a method for the high voltage switcher of an ultrasound system to generate the output that can be optionally put through a conventional linear regulator to further reduce noise ripple and allow the final high voltage output to be programmed by the system controller in various scan modes.

In yet another aspect, the present invention provides a method for the high voltage switching mode power supply of an ultrasound system to receive switching clock from a programmable clock generator without implementing a linear voltage regulator.

These and other objects and advantages of the present invention will no doubt become obvious to those of ordinary skill in the art after having read the following detailed description of the preferred embodiment, which is illustrated in the various drawing figures.

BRIEF DESCRIPTION OF FIGURES

The present invention is described in detail below with reference to the following Figures.

FIG. 1 is functional block diagram for showing the system configurations and system operations in a conventional ultrasound image scanning system.

FIG. 2 is a functional block diagram for showing a prior art high voltage power supply generator.

FIG. 3 is functional block diagram for showing another prior art high voltage generator with free running clock DC-to-DC switcher.

DESCRIPTION OF PREFERRED EMBODIMENTS

Figure 4:
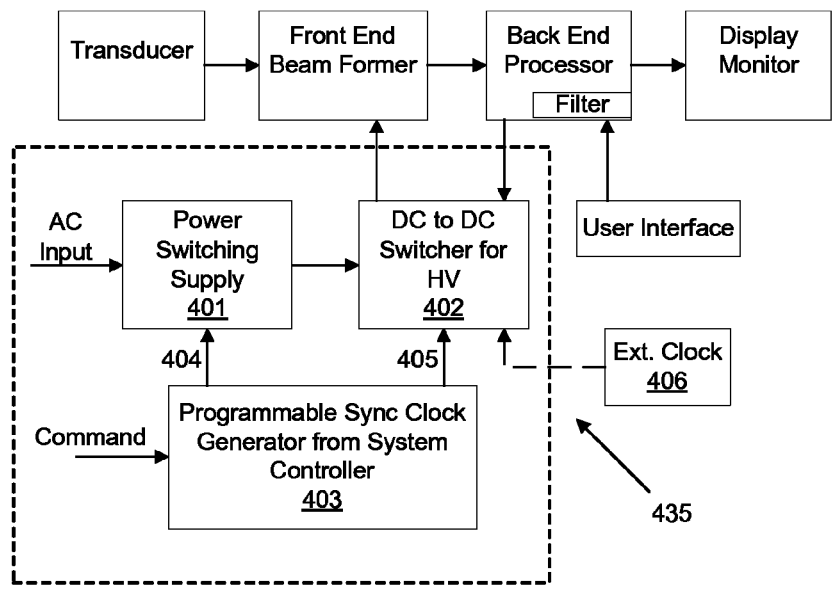
FIG. 4 a functional block diagram for showing a switching power supply and a DC-to-DC switch for high voltage generator connected to a programmable synchronization clock of this invention.

Referring to FIG. 4 for an embodiment of a voltage generator 435 of the present invention. The voltage generator includes a switching power supply 401 for generating a DC low voltage, and DC-to-DC switcher 402 for generating high voltage. The switching power-supply 401 and the DC-to-DC switching high voltage generator 402 are both connected to a programmable, sync clock generator 403. The 403 is further controlled by a system controller (not shown) to set up the synchronized clock signals 404 and 405 to the switching power supply 401 and the DC-to-DC switch high voltage generator 402 respectively. The low voltage outputs from 401 also provide low voltages, e.g., +3.3, +5, +12V, for the digital circuitry. The digital circuitry normally has higher interference immunity; therefore the implementation of an external synchronization clock 406 can be optional when the digital circuits are shielded properly.

The programmable synchronization clock generator 403 is connected to the system controller (not shown). Depending on the transmit mode and carrier frequency, the system controller sets up the programmable synchronization clock generator for providing signals to the high voltage switcher 402. The typical clock frequency is programmed from 200 KHz to 1000 KHz. Since the programmed switching clock is in synchronization with the transmit carrier, whatever beating noise in between the switching frequency (including its harmonics) and carrier can be cancelled out at the output by applying a predefined demodulation process.

Because the switching clock signals in the DC-to-DC switcher for high voltage generator 402 is in sync with the transmit carrier, every burst out carrier will have the switching glitch noise happen at the same phase, and is translate to DC after mixer demodulation. At the back end processor, the coherent interference can be conveniently removed with a simple DC high pass filter.

Figure 5:
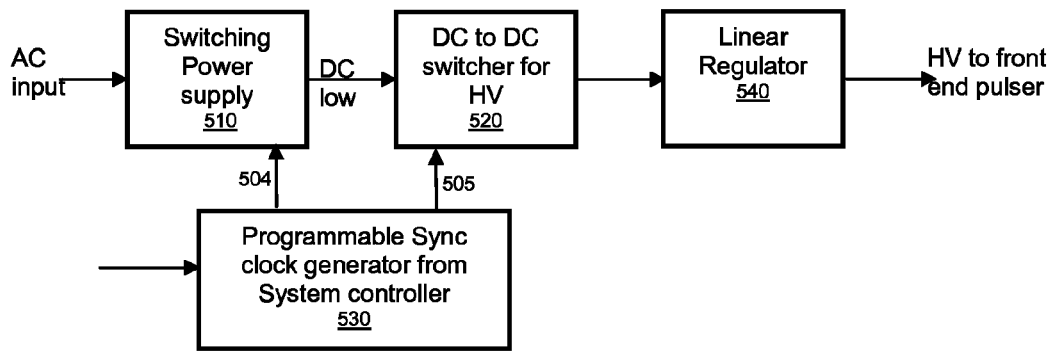
FIG. 5 is functional block diagram for showing a switching power supply and a DC-to-DC switch for high voltage generator connected to a programmable synchronization clock of this invention and connected further to a linear regulator.

FIG. 5 expands the present invention by providing a linear regulator 540 to further stabilize the high voltage output. Since the high voltage is already close to the target level, the additional linear regulator would have very minimal effect on the system efficiency.

Figure 6:
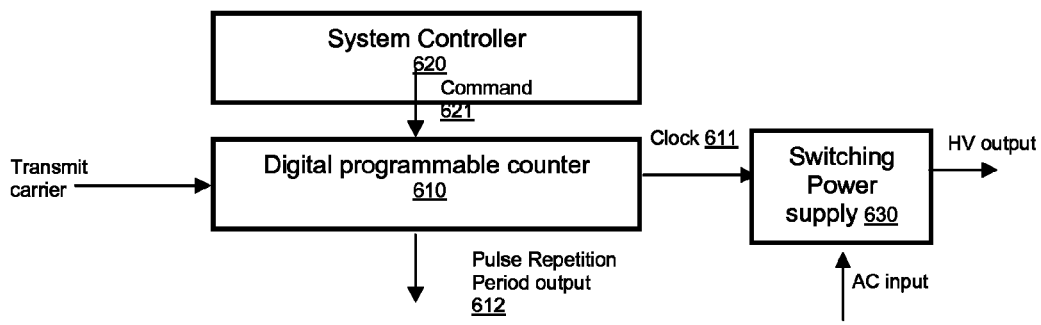
FIG. 6 is a functional block diagram for showing the functional blocks included in a programmable synchronization clock generator of this invention.

FIG. 6 is the block diagram of the programmable clock generator that includes a digital programmable counter 610. The digital programmable counter 610 receives command 621 from a system controller 620 to set up the divided down ratio. The digital programmable counter 610 also receives the transmit carrier input and applies the divide down ratio to divide and generate clock signal 611 for inputting to the switching power supply 630. The switching power supply 630 then receives the AC input and generates DC output according to the frequency of the switching clock signal 611. The programmable generator also outputs 612 as the pulse repetition period for controlling the transmit burst interval in all modes except continuous wave Doppler. Since 612 also divided down from the transmit carrier, it will also sync with the clock 611. The 612 changes when the user changes image depth in B or M mode; or burst interval in Doppler or Color mode.

According to above descriptions, this invention provides an improved method and system for a medical imaging system that uses a switching power supply with external programmable sync clock. This improved system configuration provides a method to overcome the interference problems and therefore is robust against decreased imaging performance due to interference from the power supply. Embodiments of the present invention include a method and a system for synchronizing a switching power supply clock with a medical imaging transducer working frequency. In one embodiment, synchronization of signals is assured with a programmable clock for switching power supply and also the ultrasound transmit carrier. In another embodiment, the switching clock is divided down from the carrier. Further embodiments of the present invention also include a medical imaging method and a medical imaging system that include method and system to enable control methods and signals required to accomplish frequency synchronization.

According to the embodiments of the present invention described above, there is a programmable and synchronous DC-DC Switcher for generating the high voltage power supply in an ultrasound system. The interference in this arrangement will become substantially a coherent pattern and can be substantially filtered out thus not present in the signal processing path. The interference from the high voltage switching power supply is programmable and in synchronization with the transmit carrier under different modes and different transducers, therefore will be suppressed out in the digital signal processing channel. For instance, if the switching frequency is a subset of the transmit carrier, the interference will be end up at the DC and removed by the wall motion high pass filter which has zero gain at DC frequency in Doppler processor.

In some embodiments of the present invention, the high voltage switching power supply is designed to accept an external clock signal. Then, the external clock signal provided to the power supply is generated by dividing down the transmit carrier to somewhere around the operating frequency range of the power supply (e.g., around 500 KHz) and meet the switcher's component requirement. When the user changes transducer or mode, the transmit carrier is changed, and so the sync clock frequency is also changed. Since the switching clock and it's harmonics have an integer relationship with the transmit frequency, the transmit carrier and the switching noise substantially will not generate any beating frequency other than zero hertz, or cause an extra Doppler tone when the transducer or the system is not perfectly shielded from the switching power supply.

As shown in FIGS. 4 and 5, the ultrasound systems of this invention provide new feature by implementing a programmable and synchronized clock source for the high voltage switcher. The system users have the flexibilities to use different probes with different frequencies for different applications or scan modes. With the programmable clock which is maintained in sync with the transmit carrier (integer frequency relationship), the switching clock and its harmonics will be coherent with the carrier frequency and prevent the beating frequencies to cause interfering tones.

As shown in FIG. 5, the output of the high voltage switcher can be optionally put through a linear regulator 540 to further reduce noise ripple and allow the final high voltage output to be programmed by the system controller in various scan modes.

According to above descriptions, this invention discloses a method for configuring an ultrasonic image scanning system without a linear voltage regulator thus reduces the size and weight of the ultrasonic image scanning system. The method includes a step of projecting ultrasound signals with a transmit carrier frequency for scanning an organic object. The method further includes a step of synchronizing a switching mode power supply with the transmit carrier frequency by operating the switching mode power supply with a programmable clock. In a preferred embodiment, the method further includes a step of employing a filter for removing a substantially coherent interference signal generated by the switching mode power supply synchronizing substantially with the transmit carrier frequency. In another preferred embodiment, the method further includes a step of applying a system controller for controlling the programmable clock for synchronizing clocks depending on a pulse repetition period. In an alternate embodiment, the method further includes a step of applying a system controller for controlling the programmable clock for synchronizing clocks depending on an image depth. In another embodiment, the method further includes a step of applying a system controller for controlling the programmable clock for synchronizing clocks depending on a mode setting. In another preferred embodiment, the method further includes a step of applying a system controller for controlling a digital programmable counter of the programmable clock for synchronizing clocks depending on a pulse repetition period.

The description and the drawings of the present document describe examples of embodiment(s) of the present invention and also describe some exemplary optional feature(s) and/or alternative embodiment(s). It will be understood that the embodiments described are for the purpose of illustration and are not intended to limit the invention specifically to those embodiments. Rather, the invention is intended to cover all that is included within the spirit and scope of the invention, including alternatives, variations, modifications, equivalents, and the like.

I claim:

1. A high voltage generator configured for use in an ultrasonic image scanning system for scanning an organic object by projecting ultrasound signals at a transmit carrier frequency comprising:
    a switching mode power supply;
    a direct current-to-direct current switching voltage generator in electrical communication with the switching mode power supply;
    a programmable clock comprising a transmit carrier frequency input, the programmable clock in electrical communication with the switching mode power supply and the direct current-to-direct current switching voltage generator, the programmable clock synchronized with the transmit carrier frequency and configured to synchronize the switching mode power supply and the direct current-to-direct current switching voltage generator such that a change in the transmit carrier frequency causes the programmable clock to sync the switching mode power supply to the changed transmit carrier frequency;
    a system controller configured to control said programmable clock configured for syncing upon a change in pulse repetition period in Color mode or Doppler mode; and
    a digital programmable counter, the digital programmable counter configured to receive a command from the system controller to set up a divided down ratio configured to divide and generate a switching clock signal input to the switching mode power supply.

2. The high voltage generator of claim 1, wherein:
    said switching mode power supply further comprises circuits for generating a low voltage and a high voltage.

3. The high voltage generator of claim 2 further comprising:

a transducer configured for projecting ultrasound signals, wherein said transducer is connected to and electrically excited by high voltage generated by said switching mode power supply.

4. The high voltage generator of claim 1 wherein:
said programmable clock is configured for receiving a user command for operating with said switching mode power supply in synchronization with said transmit carrier frequency.

5. The high voltage generator of claim 1 further comprising:
a linear voltage regulator configured for stabilizing and minimizing ripples in an output voltage.

6. The high voltage generator of claim 1:
wherein the system controller for controlling said programmable clock is configured for syncing upon a change in an image depth.

7. The high voltage generator of claim 1:
wherein the system controller for controlling said programmable clock is configured for syncing upon a change in a mode setting.

8. The high voltage generator of claim 1 further comprising:
a filter for removing a substantially coherent interference signal generated by said switching mode power supply synchronizing substantially with said transmit carrier frequency.

9. A method for configuring a high voltage generator for use in an ultrasonic image scanning system having a switching mode power supply, comprising:
generating an ultrasound signal at a transmit carrier frequency for scanning an organic object;
receiving the transmit carrier frequency by a digital programmable counter;
applying a divide down ratio by the digital programmable counter to the transmit carrier frequency to generate input to the switching mode power supply,
synchronizing the switching mode power supply with said transmit carrier frequency by controlling said switching mode power supply with a programmable clock such that a change in the transmit carrier frequency causes the programmable clock to sync the switching mode power supply to the changed transmit carrier frequency; and
controlling, by a system controller, said programmable clock for syncing upon a change in pulse repetition period in Color mode or Doppler mode.

10. The method of claim 9 further comprising:
employing a filter for removing a substantially coherent interference signal generated by said switching mode power supply synchronizing substantially with said transmit carrier frequency.

* * * * *